United States Patent [19]

Huellmann et al.

[11] Patent Number: 5,120,880

[45] Date of Patent: Jun. 9, 1992

[54] PREPARATION OF MUSCONE, INTERMEDIATES FOR THIS PREPARATION AND PREPARATION OF SAID INTERMEDIATES

[75] Inventors: Michael Huellmann, Heppenheim; Thomas Kuekenhoehner, Frankenthal; Karl Brenner, Ludwigshafen; Rainer Becker, Bad Durkheim; Matthias Irgang, Heidelberg; Charles Schommer, Ludwigshafen, all of Fed. Rep. of Germany

[73] Assignee: BASF Atkiengesellschaft, Ludwigshafen, Fed. Rep. of Germany

[21] Appl. No.: 757,305

[22] Filed: Sep. 10, 1991

Related U.S. Application Data

[62] Division of Ser. No. 524,929, May 18, 1990, Pat. No. 5,081,311.

[30] Foreign Application Priority Data

Jun. 2, 1989 [DE] Fed. Rep. of Germany ....... 3918015

[51] Int. Cl.⁵ ............................................ C07C 49/203
[52] U.S. Cl. .................................................. 568/412
[58] Field of Search ........................................ 568/412

[56] References Cited

PUBLICATIONS

Tsuji et al., Chem. Lett; 1976, (7) pp. 773-774.

Primary Examiner—James H. Reamer
Attorney, Agent, or Firm—Oblon, Spivak, McClelland, Maier & Neustadt

[57] ABSTRACT

Muscone of the formula I

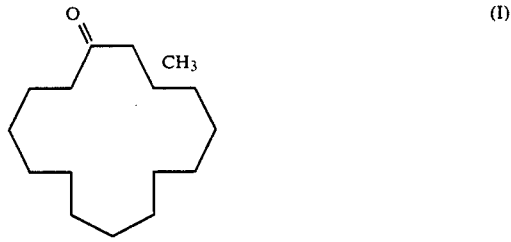

is prepared by a process in which an open-chain 2,15-diketone of the general formula II $$CH_3-CO-X-CO-CH_3 \qquad (II)$$

where
X is one of the radicals $$-(-CH_2-)_{12}- \qquad (a)$$

$$-CH=CH-(-CH_2-)_8-CH=CH- \qquad (b)$$

$$-CH_2-CH=CH-(-CH_2-)_6-CH=CH-CH_2- \qquad (c)$$

$$-CH_2-CH_2-CH=CH-(-CH_2-)_4-CH=CH-CH_2-CH_2- \qquad (d)$$

or $$-CH_2-CH_2-CH_2-CH=CH-(-CH_2-)_2-CH=CH-CH_2-CH_2-CH_2- \qquad (e)$$

is brought into contact, at from 300° to 400° C. in the presence of from 5 to 15% by weight, based on the amount of catalyst, of water, in the gas phase, with a fixed-bed catalyst containing $TiO_2$, $CeO_2$ or $ThO_2$ as the catalytically active compound and the unsaturated cyclic ketone formed by intramolecular aldol condensation is subjected to catalytic hydrogenation. Furthermore, the open-chain unsaturated ketones of the formulae IIb, IIc and IId and advantageous processes for their preparation and their use as intermediates for a simple industrial synthesis of muscone are claimed.

1 Claim, No Drawings

PREPARATION OF MUSCONE, INTERMEDIATES FOR THIS PREPARATION AND PREPARATION OF SAID INTERMEDIATES

This is a division of application Ser. No. 524,929, filed on May 18, 1990 now U.S. Pat. No. 5,081,311.

The present invention relates to a process for the preparation of the desirable scent muscone by intramolecular aldol condensation of hexadecane-2,15-dione or a hexadecadiene-2,15-dione in the gas phase, and novel hexadecadiene-2,15-diones and an advantageous process for their preparation.

Muscone (3-methylcyclopentadecanone) of the formula I

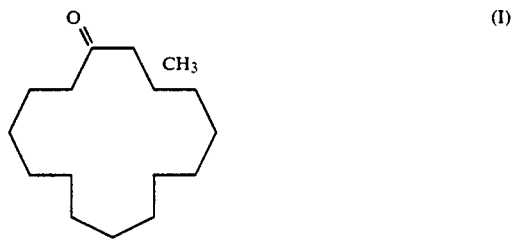

is one of the most important ingredients of the natural musk extracts which are very desirable in perfumery. Because of the extremely high price of natural extracts, the synthesis of I is of considerable interest, particularly since I is far superior to all known musk scents, such as the tetralin and nitromusk compounds.

The preparation methods used to date are predominantly based on ring enlargement reactions, starting from cyclododecanone (cf. for example Helv. Chim. Acta 71 (1988), 1704–1718, and in the literature stated in loc. cit). These methods all involve multistage steps, some of which are very expensive, and are therefore unattractive for commercial use.

Other known synthesis methods involve intramolecular condensation reactions, such as aldol, Dieckmann and acyloin condensation (cf. Houben-Weyl, Methoden der organischen Chemie, Vol. 4/2, page 729–815). All these methods have the great disadvantage that relatively good yields of macrocycles are obtained only at very high dilution.

Helv. Chim. Acta, 62 (1979), 2673–2680 presents a novel synthesis method for muscone based on 4,8 dodecadienediol. The key step here is the acid-catalyzed intramolecular cyclization of an open-chain hydroxyacetal to the bicyclic dihydropyran; however, owing to the necessary dilution principle, large amounts of solvent are required, with the result that this process is suitable only for the synthesis of laboratory quantities.

A possible method for the preparation of I, which in principle is a very good one, appeared to be the aldol condensation first described by Stoll (cf. Helv. Chim. Acta, 30 (1947), 2019–2023), starting from hexadecane-2,15-dione of the formula IIa $$CH_3-CO-(CH_2)_{12}-CO-CH_3 \qquad (IIa)$$

since here the methyl group in the 3-position of I is simultaneously introduced.

However, this process had notable disadvantages:
1) The possibilities for the preparation of the ketone of the formula IIa required as a starting material or of adequate 2,15-diketones have been unsatisfactory to date.
2) The yields obtainable in the aldol condensation are relatively low, despite the use of highly dilute solutions (17% according to loc. cit.).

Regarding 1, there has in the past therefore been no lack of attempts to develop suitable preparation methods for IIa. Stoll synthesized it in accordance with the following equation:

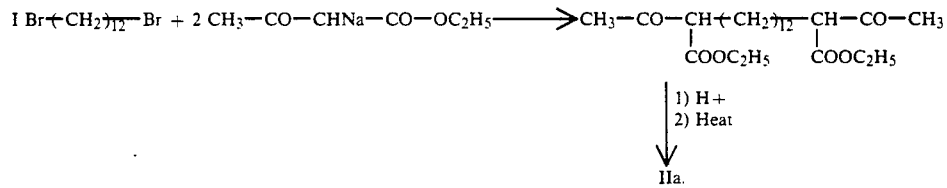

The particular disadvantage of the synthesis is the use of the expensive and also toxicologically unacceptable 1,10-dibromodecane.

Furthermore, J. Am. Chem. Soc. 82 (1960), 1447–1450 presents the following synthesis, starting from 2,2′,5′,2″-terthienyl:

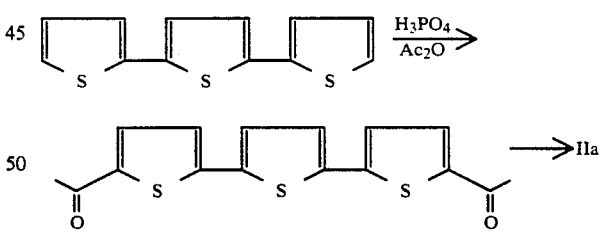

For the synthesis of larger amounts of diketone, however, this synthesis is unsuitable owing to the poor availability of the starting material.

Two further processes for the preparation of the diketone IIa, each starting from butadiene, have been described by Tsugi et al.:

a) In Chem. Lett. 1976, pages 773–774:

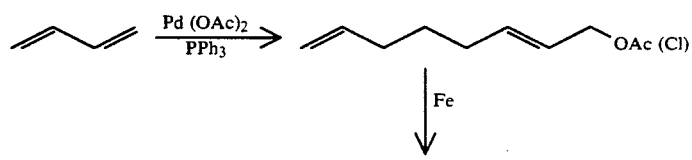

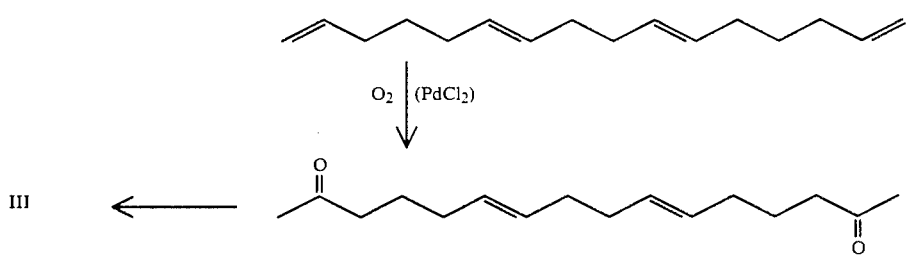

and
b) in Bull. Chem. Soc. Japan, 51 (1978), 1915:

$CH_3-C-CH_2-CH=CH-(CH_2)_6CH=CH-CH-$

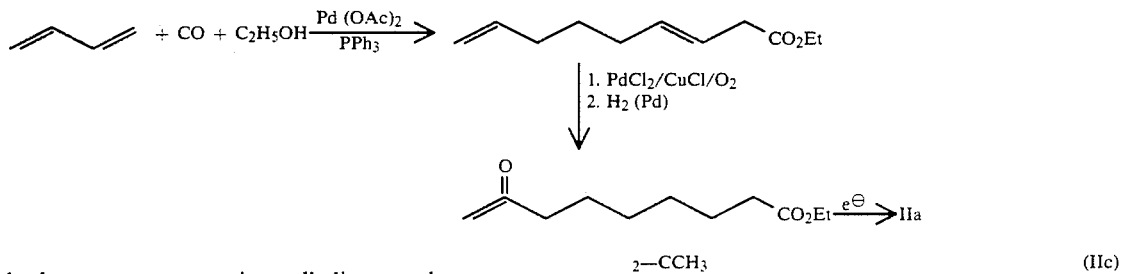

In both processes, expensive palladium catalysts are used, with the result that these syntheses too are unattractive for industrial use.

Furthermore, Bull. Chem. Soc. Japan, 56 (1983), 345–346 discloses a process for the preparation of IIa starting from α,Ω-tetradecanedicarboxylic acid. The disadvantage of this process is the poor availability of the starting compound.

J. Organomet. Chem. 264 (1984), 229–237 furthermore discloses a process for the preparation of IIa starting from $(CH_3)_3Si-CH_2-CH=CH-CH_2-CH_2-C(CH_3)=CH-CH_2-Si(CH_3)_3$. The disadvantage of this process is the poor availability of the starting compound as well as the necessity of using problematic reagents, such as readily ignitable potassium hydride.

It is an object of the present invention to provide a technically simple and cheap method for the preparation of hexadecane-2,15-dione.

We have found that this object is achieved by providing the novel diunsaturated 2,15-diketones of the general formula II $CH_3-CO-X-CO-CH_3$      (II)

where X is a straight-chain alkadienylene radical of the structure $-CH=CH-(CH_2)_8CH=CH-$      (b)

$-CH_2-CH=CH-(CH_2)_6CH=CH-CH_2-$      (c)

$-CH_2-CH_2-CH=CH-(CH_2)_4CH=CH-CH_2-CH_2-$      (d)

since these 2,15-diketones can be prepared in a technically simple manner on the one hand and, on the other hand, can be very advantageously converted into the diketone IIa and into muscone.

The present invention therefore also relates to a process for the preparation of a mixture of the diunsaturated 2,15-diketones of the formulae IIb and IIc $CH_3-CO-CH=CH-(CH_2)_8CH=CH-CO-CH_3$      (IIb)

$2-CCH_3$      (IIc)

wherein 1,10-decanediol of the formula III $OH-CH_2-(CH_2)_8CH_2-OH$      (III)

is dehydrogenated under oxidative conditions, the resulting 1,10-decanedial of the formula IV $OHC-(CH_2)_8CHO$      (IV)

is subjected to a Wittig reaction with 2 moles of a 2-oxopropenyltriphenylphosphonium salt of the formula V

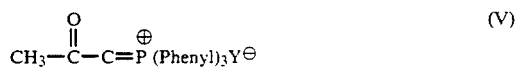

where $Y^\ominus$ is $Cl^\ominus$, $Br^\ominus$ or $HSO_4^\ominus$, and the reaction product is distilled.

The 1,10-decanediol required for this process is a commercial compound which can be obtained in a relatively simple manner by alkaline cleavage of castor oil and subsequent hydrogenation of the resulting sebacic acid.

The oxidative dehydrogenation of 1,10-decanediol to give 1,10-decanedial can be carried out in various ways. Advantageously, the reaction is carried out in the gas phase over silver catalysts, as described, for example, in Manuf. Chem. Aerosol News 37 (1966), 42–45, for $C_5$–$C_{14}$-alcohols. Further details of the reaction conditions for this process stage can be found in the stated literature. However, it can also be carried out by oxidation in methylene chloride using aqueous NaOCl solution, in the presence of a catalytic amount of 4-methoxy-2,2,6,6-tetramethylpiperidine N-oxide. For further details of this process stage, reference may be made to J. Org. Chem. 52 (1987), 2559–2562.

To carry out the Wittig reaction with a 2-oxopropenyltriphenylphosphonium salt of the formula V, the following procedure is advantageously adopted: the said salt in an inert organic solvent, such as methylene chloride, is initially taken, and the solution of the 1,10-dial in an inert solvent, preferably the same inert solvent, is added slowly, and the reaction mixture is stirred for a further 1-2 hours.

Working up is effected in the conventional manner for Wittig reactions, by evaporating down the mixture, precipitating the phosphine oxide and carrying out distillation. $^{13}$C-NMR investigations have shown that, when the reaction mixture is worked up by distillation, some of the initially formed diketone of the formula IIb is isomerized to the diketone of the formula IIc.

The present invention also relates to a process for the preparation of the diunsaturated 2,15-diketone of the formula IId $$CH_3-CO-CH_2-CH_2-CH=CH-(CH_2)_4CH=CH-CH_2-CH_2-CO-CH_3 \quad (IId)$$

wherein

A. 1,6-hexanediol of the formula VI $$HO-CH_2-(CH_2)_4CH_2-OH \quad (VI)$$

is dehydrogenated under oxidative conditions,

B. the resulting adipodialdehyde of the formula VII $$OHC-(CH_2)_4CHO \quad (VII)$$

is reacted with 2 moles of a vinylmagnesium halide of the formula VIII $$CH_2=CH-Mg-Hal \quad (VIII)$$

where Hal is Cl or Br, in a Grignard reaction, and the resulting 1,9-decadiene-3,8-diol of the formula IX $$CH_2=CH-\underset{|}{\overset{OH}{C}}H-(CH_2)_4\underset{|}{\overset{OH}{C}}H-CH=CH_2 \quad (IX)$$

is subjected to a Carroll reaction with an alkyl acetoacetate.

The 1,6-hexanediol required for this process is a starting compound which is available industrially on a large scale and is therefore cheap.

The oxidative dehydrogenation of the 1,6-hexanediol to the adipodialdehyde can be carried out, for example, similarly to the oxidative dehydrogenation, described above, of the 1,10-decanediol in the gas phase over a silver catalyst or using aqueous NaOCl solution in the presence of 4-methoxy-2,2,6,6-tetramethylpiperidine N-oxide.

The subsequent vinylation with 2 moles of a vinylmagnesium salt is carried out in a manner conventionally used for Grignard reactions. For example, the vinylmagnesium halide is prepared, and initially taken, in a solvent, such as tetrahydrofuran (THF), and a solution of the adipodialdehyde in THF is slowly added while the temperature is monitored. Conventional working up and fractional distillation give 1,9-decadiene-3,8-diol of the formula IX in very good yields. For further details of this reaction step, reference may be made to Bull. Soc. Chim. France 1959, pages 1248-1251, in particular 1248.

The Carroll reaction of 1,9-decadiene-3,8-diol with an alkyl acetoacetate or preferably with methyl acetoacetate, is carried out by slowly heating both reactants to about 200° C. Elimination of methanol and subsequent elimination of CO$_2$ begin at about 160° C.

For further details of the Carroll reaction, i.e. the addition reaction of α,β-unsaturated alcohols with compounds having an active methylene group, reference may be made to Chem. Soc. Chim. France 1940, pages 704-706.

The novel diunsaturated 2,15-diketones of the formulae IIb to IId can, like the known diketone IIe, be converted in a simple manner and in good yields, for example by catalytic hydrogenation over a palladium catalyst, into the saturated 2,15-hexadecanedione of the formula IIa.

Regarding 2, we have found that, in the intramolecular aldol condensation of 2,15-hexadecanedione of the formula IIa, yields of up to 60% of theory can be obtained if this aldol condensation is carried out not in highly dilute solution, as is the usual procedure, but at from 300° to 450° C. and in the presence of a small amount of water in the gas phase over a fixed-bed catalyst containing TiO$_2$, CeO$_2$ or ThO$_2$, preferably TiO$_2$, as a catalytically active compound. It was very surprising that this long investigated and sensitive reaction takes place in such an extremely advantageous manner under the drastic conditions of a gas-phase reaction.

Although a gas phase cyclization reaction, i.e. the cyclization of dimethyl octadecanedioate to cycloheptadecanone, was already known, the desired cyclization product was obtained in yields of only 14% of theory, determined by gas chromatography (cf. Perfumer and Flavorist, 7 (1982), 57). The main product of this cyclization reaction was polymeric material.

Surprisingly, we have furthermore found that the diunsaturated 2,15-diketones of the formulae IIb to IIe can also be cyclized in good yields in the gas phase over catalysts containing TiO$_2$, CeO$_2$ or ThO$_2$ as the catalytically active compound.

This was particularly surprising since J. Organometallic Chem. 264 (1984), 229-237, in particular 234, discloses that, in an experiment to cyclize the 2,15-diketone of the formula IIe in the known manner with diisobutylaluminum hydride, phenol and pyridine, yields of only about 6% of theory of the corresponding cyclic ketone could be obtained.

The present invention therefore relates in particular to a process for the preparation of muscone of the formula I (I)

wherein an open-chain 2,15-diketone of the general formula II $$CH_3-CO-X-CO-CH_3 \quad (II)$$

where X is one of the radicals $$-(CH_2)_{12}- \quad (a)$$

$$-CH=CH-(CH_2)_8CH=CH- \quad (b)$$

$$-CH_2-CH=CH-(CH_2)_6CH=CH-CH_2- \quad (c)$$

—CH$_2$—CH$_2$—CH=CH—(CH$_2$)$_4$CH=CH—CH$_2$—CH$_2$—  (d)

or

—CH$_2$—CH$_2$—CH$_2$—CH=CH—(CH$_2$)$_2$CH=CH—CH$_2$—CH$_2$—CH$_2$—  (e)

is brought into contact, at from 300° to 400° C., preferably from 350° to 380° C., in the presence of from 5 to 15% by weight, based on the amount of catalyst, of water, in the gas phase, with a fixed-bed catalyst containing TiO$_2$, CeO$_2$ or ThO$_2$ as the catalytically active compound, preferably a TiO$_2$ catalyst, and the unsaturated cyclic ketone formed by intramolecular aldol condensation is subjected to catalytic hydrogenation.

The novel aldol condensation takes place particularly advantageously if the 2,15-diketones of the general formula II are brought into contact with a TiO$_2$ catalyst doped with an alkali metal oxide or alkaline earth metal oxide.

Since the 2,15-diketones of the general formula II can be prepared in a technically simple manner by the process described above, there is thus a technically simple and advantageous synthesis route to the desirable musk scent muscone.

The intramolecular aldol condensation is carried out in the gas phase at from 300° to 400° C., preferably from 350° to 390° C., in particular from 350° to 380° C. TiO$_2$, in particular TiO$_2$ doped with alkali metal oxides or alkaline earth metal oxides, i.e. TiO$_2$ containing about 2-10% by weight of Na$_2$O and/or K$_2$O, is particularly advantageously used as the catalyst for the novel process. The catalysts described may be used, for example, in the form of 2-4 mm extrudates or in the form of pellets having a diameter of 3-4 mm. In the reaction in the gas phase, a space velocity of from 0.1 to 30, in particular from 1 to 10, g of open-chain diketone of the formula II per g of catalyst per hour is advantageously maintained.

To carry out the reaction, in general a solution of the diketone of the formula II, obtained in crystalline form, in an inert organic solvent such as toluene or a xylene, is first vaporized in a tube reactor and then passed, if necessary together with an inert gas, such as carbon dioxide or nitrogen, at the desired reaction temperature in gaseous form over the fixed-bed catalyst. In order to obtain good yields of cyclic ketone, it is still necessary to add small amounts of water in order to prevent possible coking of the catalyst. Advantageously, from 5 to 15% by weight, based on the amount of catalyst, of water are used.

The reaction products are condensed by means of suitable cooling apparatuses and are investigated by gas chromatography. Reaction products containing unconverted starting material can, if required, be recycled directly to the cyclization reaction, without further purification.

The unsaturated cyclic ketones of the formulae Xa to Xc which are obtained in this aldol condensation are then converted into the desired musk scent muscone in a conventional manner by hydrogenation in the presence of a Pd catalyst.

With the aid of the novel intramolecular aldol condensation of the 2,15-diketones of the formula II and the subsequent catalytic hydrogenation, it is possible to obtain the desirable musk scent muscone in excellent yields. By providing the novel 2,15-diketones of the formulae IIb to IId and advantageous processes for their preparation, there is thus a technically simple and advantageous synthesis route from readily available starting materials to the desirable compound muscone.

EXAMPLE 1 a) Preparation of adipodialdehyde (VII)

The following chemicals were initially taken in a 4 l three-necked flask at room temperature (RT):

59 g (0.5 mole) of 1,6-hexanediol
3.9 g (0.025 mole) of 2,2,6,6-tetramethylpiperidine 1-oxide
3.0 g (0.025 mole) of KBr
7.8 g (0.05 mole) of NaH$_2$PO$_4$.2H$_2$O
8.9 g (0.05 mole) of NaH$_2$PO$_4$.2H$_2$O
1 l of CH$_2$Cl$_2$ + 375 ml of water.

567 g (0.51 mole) of a roughly 13% strength aqueous NaOCl solution were then added dropwise in the course of 2 hours (h), a slightly exothermic reaction taking place. During this, the pH of the reaction solution changed from 6.7 to 6.0. After the dropwise addition, stirring was continued for 15 minutes (min) at RT. The organic phase was separated off, after which the aqueous phase was extracted with twice 200 ml of CH$_2$Cl$_2$ and the combined organic phases were washed neutral with NaHCO$_3$ solution and dried with Na$_2$SO$_4$. After Na$_2$SO$_4$ had been filtered off, the solvent was distilled off in a rotary evaporator and a gas chromatogram of the residue was recorded.

The crude product was vinylated directly in the next stage.

b) Preparation of 1,9-decadiene-3,8-diol (IX)

0.81 l of a 1.55 molar vinylmagnesium chloride solution in tetrahydrofuran (THF) was initially taken. 48.0 g of adipodialdehyde (crude, 80.5% strength), dissolved in 50 ml of THF, were added dropwise in the course of 1 h while monitoring the temperature, after which stirring was continued for 2 hours. After the usual working up procedure, 59.6 g of a pale yellow oil remained, which was subjected to fractional distillation under greatly reduced pressure (oil pump).

The yield after distillation (bp.=108°-110° C./0.5) was 36.4 g (91% strength), corresponding to a yield of 64% of theory.

c) Preparation of 5,11-hexadecadiene-2,15-dione (IId)

A mixture of 36.4 g of a 91% strength (corresponding to 0.19 mole) of 1,9-decadiene-3,8-diol and 74.5 g (0.61 mole) of methyl acetoacetate was heated to 200° C. in the course of 3 h. At about 160° C., elimination of methanol began, followed by elimination of $CO_2$. A total of 14.1 g of low boilers (bp.<70° C.) distilled off, and 9.5 l of $CO_2$ (theory 10.2 l) were eliminated. The residue (73.5 g) was then subjected to fractional distillation under greatly reduced pressure (oil pump).

The yield after distillation (bp.=160°-170° C./0.5) was 38.6 g (81% strength), corresponding to a yield of 66% of theory. The melting point was 54° C.

$^1$H-NMR (CDCl$_3$): $\delta$=1.32 (4H, m); 1.8-2.0 (4H, m); 2.1 (6H, s); 2.2-2.3 (4H, m); 2.5 (4H, b); 5.3-5.4 (4H, m);

$^{13}$C-NMR (CDCl$_3$): $\delta$=26.9; 28.9; 29.6; 32.3; 43.6; 128.6; 131.3; 207.4.

d) Preparation of hexadecane-2,15-dione 38 g of hexadeca-5,11-diene-2,15-dione (0.152 mole) were dissolved in 200 ml of ethyl acetate and hydrogenated at 50° C. under standard conditions using 1.9 g of 10% strength Pd/C. Recrystallization from petroleum ether gave 25.8 g of a 97% strength hexadecane-2,15-dione of melting point 80° C. The yield was thus 66% of theory.

EXAMPLE 2 a) Preparation of 1,10-decanedial (IV)

37 g (0.2 mole) of 1,10-decanediol were converted into 1,10-decanedial by oxidation using a process similar to that of Example 1a). The yield was 31 g (79% strength), corresponding to 73% of theory.

b) Preparation of 3,13-hexadecadiene-2,15-dione (IIb) and 5,11-hexadecadiene-2,15-dione (IIc)

1150 ml of a 0.783 molar solution of triphenylphosphine-2-oxopropylene in dichloromethane (0.9 mole) were initially taken at RT. A solution of 69.5 g of 1,10-decanedial (0.33 mole) in 250 ml of dichloromethane was added dropwise to the resulting Wittig reagent in the course of 2 h (slightly exothermic reaction) and stirring was continued for a further hour. For working up, the content of the flask was evaporated down and the residue was stirred thoroughly with 1 l of cyclohexane. The phosphine oxide which crystallized out was filtered off, and the mother liquor was stirred again with 300 ml of cold cyclohexane. After the residual amount of phosphine oxide had been separated off, the mother liquor was evaporated down and the residue was subjected to fractional distillation under reduced pressure (oil pump).

The yield of 3,13-hexadecadiene-2,15-dione of boiling point 136°-139° C./0.03 mm was 72 g (93% strength), corresponding to a yield of 81% of theory.

$^{13}$C-NMR (CDCl$_3$): $\delta$= 197.4 (C-2, C-15); 147.6 (C-4, C-13); 131.4 (C-3, C-14); 32.3 (C-5, C-12); 29.2 (C-8, C-9); 29.1 (C-7, C-10); 28.2 (C-6, C-11), 26.7 (C-1, C-16).

Evaluation of the $^{13}$C-NMR data for the reaction products showed that, during distillation, 25% of the resulting compound of the formula IIb are isomerized to the compound of the formula IIc.

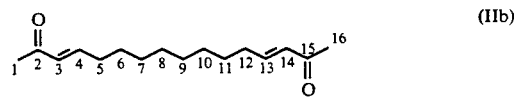
(IIb)

$^{13}$C—NMR (CDCl$_3$): $\delta$=206.0 (C-2, C-15); 134.9 (C-5); 122.3 (C-4); 47.5 (C-3); 32.4 (C-6); 28.6 (C-7).

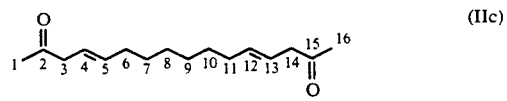
(IIc)

EXAMPLES 3 TO 8

A solution of 1.5 g of a hexadecane-2,15-dione (IIa) obtained according to Example 1, in a mixture of 20 ml of decalin and 10 ml of toluene, was vaporized in a tube reactor and then passed, together with nitrogen, at the reaction temperature stated in the Table, in gaseous form over a catalyst which was arranged as a fixed bed in a column (d=22 mm, length=50 cm), had the composition shown in the Table and was in the form of 2-4 mm extrudates. In Examples 1 to 4, the amount of water shown in the Table was also added to the reaction mixture.

The reaction products were condensed by means of a suitable cooling apparatus, investigated by gas chromatography and then hydrogenated in the presence of Pd catalysts.

The reaction conditions and the experimental results obtained are summarized in the Table below.

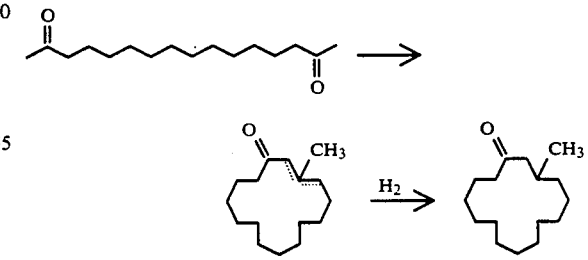

TABLE

| Example | Catalyst | Addition of water [ml/h] | Reaction temperature [°C.] | LHSV [10 L N$_2$/h; 1.5 g IIa in 20 ml decalin + 10 ml toluene/h] | Conversion | Selectivity of the muscone formation |
|---|---|---|---|---|---|---|
| 3 | TiO$_2$ + 2% Na$_2$O | 5 | 350 | 0.01 | 51.3 | 70.5 |

TABLE-continued

| Example | Catalyst | Addition of water [ml/h] | Reaction temperature [°C.] | LHSV [10 L N$_2$/h; 1.5 g IIa in 20 ml decalin + 10 ml toluene/h] | Conversion | Selectivity of the muscone formation |
|---|---|---|---|---|---|---|
| 4 | TiO$_2$ + 2% Na$_2$O | 5 | 370 | 0.01 | 62.6 | 86.7 |
| 5 | TiO$_2$ + 2% Na$_2$O | 15 | 380 | 0.01 | 53.4 | 49.6 |
| 6 | TiO$_2$ + 2% Na$_2$O | 15 | 400 | 0.01 | 96.6 | 19.3 |
| 7 | TiO$_2$ + 2% Na$_2$O | — | 370 | 0.01 | 100 | 7.8 |
| 8 | TiO$_2$ | 5 | 370 | 0.01 | 82.3 | 57.5 |

EXAMPLE 9

A solution of 4.5 g of a 5,11-hexadecadiene-2,15-dione IId prepared similarly to Example 1a to c, in 20 ml of toluene, was evaporated per hour (LHSV=0.03) in a tube reactor with the addition of 5 ml of water per hour and was passed, together with 10 l of N$_2$ per hour and at 380° C., in gaseous form over a catalyst which was arranged as a fixed bed in a column (d=22 mm, l=50 cm), consisted of TiO$_2$ and 2% of Na$_2$O and was in the form of 2-4 mm extrudates. The reaction products were condensed by means of a suitable cooling apparatus and then investigated by gas chromatography.

A hexahydromuscone selectivity of 63% of theory was obtained at a conversion of 66%.

We claim:

1. An open-chain diunsaturated 2,15-diketone of the formula II $$CH_3—CO—X—CO—CH_3 \qquad (II)$$

where X is a straight-chain alkadienylene radical of the structure $$—CH=CH—(—CH_2—)_8—CH=CH— \qquad (b)$$

$$—CH_2—CH=CH—(—CH_2—)_6—CH=CH—CH_2— \qquad (c)$$

or $$—CH_2—CH_2—CH=CH—(—CH_2—)_4—CH=CH—CH_2—CH_2— \qquad (d).$$

* * * * *